United States Patent [19]

Suzuki et al.

[11] 4,082,913
[45] Apr. 4, 1978

[54] PHENOXYALICYCLIC CARBOXYLIC ACID DERIVATIVES

[75] Inventors: Yoshio Suzuki, Itami; Masayoshi Minai, Moriyama; Noritaka Hamma, Sakai; Eiichi Murayama, Takarazuka; Shunji Aono, Toyonaka, all of Japan

[73] Assignee: Sumitomo Chemical Company, Limited, Osaka, Japan

[21] Appl. No.: 365,277

[22] Filed: May 30, 1973

[30] Foreign Application Priority Data

Jun. 1, 1972 Japan .................................. 47-54849

[51] Int. Cl.² .............................................. C07C 69/76
[52] U.S. Cl. ................... 560/102; 260/520 B; 424/308; 424/317
[58] Field of Search ............................ 260/473 G, 520

[56] References Cited

U.S. PATENT DOCUMENTS

| | | | |
|---|---|---|---|
| 2,370,256 | 2/1945 | Niederl | 260/520 |
| 3,097,139 | 7/1963 | Thorp | 260/521 R |
| 3,262,850 | 7/1966 | Jones et al. | 260/473 G |
| 3,332,957 | 7/1967 | Bencze | 260/473 G |
| 3,546,273 | 12/1970 | Bolhofer | 260/473 G |
| 3,716,583 | 2/1973 | Nakamura et al. | 260/520 |
| 4,008,265 | 2/1977 | Suzuki et al. | 560/57 |

Primary Examiner—Paul J. Killos
Attorney, Agent, or Firm—Stevens, Davis, Miller & Mosher

[57] ABSTRACT

Novel anti-atherosclerosis agents having the formula,

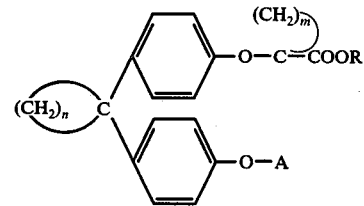

wherein R is hydrogen or lower alkyl, $n$ and $m$ each signify an integer of 4 – 6, and A is hydrogen or a group of the formula,

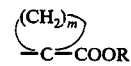

wherein R and $m$ have the same meanings as defined above.

These compounds are produced, for example, by reacting a bisphenolic compound of the formula,

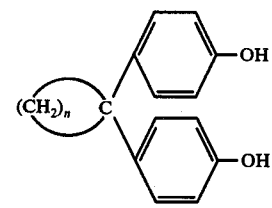

with chloroform and a ketone compound of the formula,

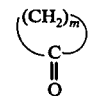

in the presence of an alkali. Alternatively, they are produced by reacting the bisphenolic compound with α-halogeno- or α-hydroxycarboxylic acid derivative of the formula,

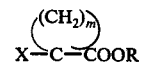

wherein R and $m$ have the same meanings as defined above, and X is halogen or hydroxyl.

1 Claim, No Drawings

PHENOXYALICYCLIC CARBOXYLIC ACID DERIVATIVES

This invention relates to novel anti-atherosclerosis agents. More particularly, the invention pertains to novel agents which are useful for the lowering of elevated levels of cholesterol or lipids.

Atherosclerosis is an adult disease for which there is no known satisfactory cure. Although the cause for atherosclerosis is not yet known in spite of discussions in the academic circles, it has broadly been recognized that one of the most significant histopathological manifestations of atherosclerosis is the deposition of lipids in the blood. Accordingly, research has been directed to the disturbed metabolism of lipids, and attention has been given to the extraordinarily elevated level of cholesterol in the blood.

A number of experimental and clinical facts have been reported, which indicate the relationship between atherosclerosis and elevated blood cholesterol or lipid level. Hence, the development of agents to reduce the elevated blood cholesterol or lipid level is considered extremely important for the prevention of atheroclerosis.

Concentrated efforts have heretofore been made for the development of such agents for lowering cholesterol or lipids and a number of compounds have been tested clinically, but none of them have been proved to be completely satisfactory. Some of them are fairly effective but produce significantly harmful side effects, and others have inadequate effectiveness, so that they are required to be administered in large doses.

A group of compounds practically employed presently for the above purpose includes ethyl α-(p-chlorophenoxy)isobutyrate. However, its effectiveness is not very high, and it has a tendency to produce harmful side effects such as hypertrophy of the liver.

The present inventors have found a group of novel compounds which are effective as cholesterol-lowering agents and which are substantially nontoxic.

It is therefore an object of the present invention to provide cholesterol- or lipid-lowering agents.

Another object is to provide a process for preparing cholesterol- or lipid-lowering agents.

A further object is to provide pharmaceutical compositions containing such agents.

Other objects will be apparent from the following description.

In order to accomplish the above objects, the present invention provides novel phenoxy alicyclic carboxylic acid derivatives of the formula,

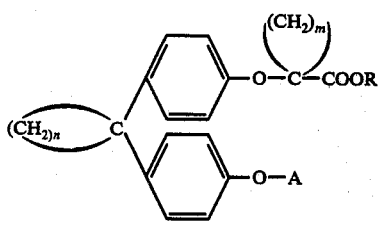

(I)

wherein R is hydrogen or $C_1$–$C_4$ alkyl, $n$ and $m$ each signify an integer of 4 to 6, and A represents hydrogen or a group of the formula,

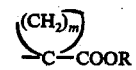

wherein R and $m$ have the same meanings as defined above.

Examples of R include methyl, ethyl, n-propyl, iso-propyl, n-butyl, iso-butyl and t-butyl.

These phenoxy alicyclic carboxylic acid derivatives (I) may be prepared by any of the procedures as shown by the following reaction scheme:

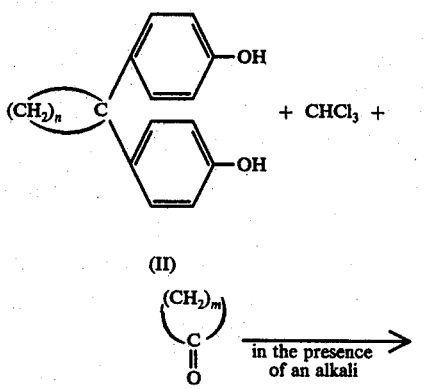

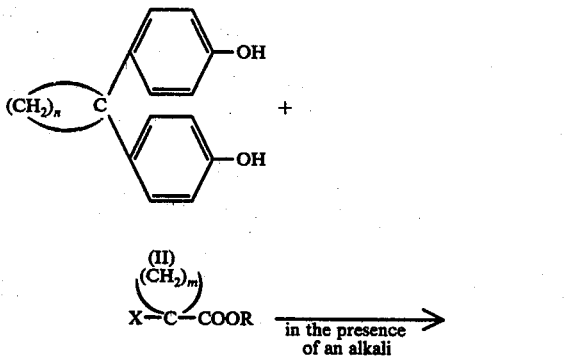

wherein X is halogen or hydroxyl, A, R, $n$ and $m$ have the same meanings as defined above; and A' is hydrogen or a group of the formula,

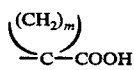

wherein $m$ have the same meanings as defined above.

The above procedures are illustrated in detail as follows:

Procedure 1

Reaction of a bisphenol derivative (II) with chloroform and a keto-compound (III) in the presence of an alkali In order to carry out the reaction of this procedure, at least 1 mole of chloroform is added dropwise into a mixture containing 1 mole of a bisphenol derivative (II) and at least 1 mole of a keto-compound (III) in the presence of at least 3 moles of an alkali. Examples of the alkali used include sodium hydroxide and potassium hydroxide. The reaction requires a temperature of 15° – 150° C, and ordinarily a temperature of 15° – 70° C, and a reaction time of 3 – 40 hours. In order to obtain as the main product one of either a phenoxy alicyclic monocarboxylic acid derivative (Ia) (i.e., A' = H) or a phenoxy alicyclic dicarboxylic acid derivative (Ia) (i.e.,

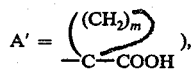

the reaction conditions such as the proportions of the reactants used, the reaction temperature and the reaction time should be carefully controlled. When about 1 mole of the keto-compound (III), about 1 mole of chloroform and about 3 moles of the alkali are used per 1 mole of the bisphenol derivative (II), a phenoxy alicyclic monocarboxylic acid derivative (Ia) (i.e., A' = H) is obtained as the main product. On the other hand, when the keto-compound, chloroform and the alkali are used in excessive amount, a bisphenoxy alicyclic dicarboxylic acid derivative (Ia), (i.e.,

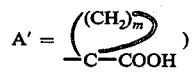

is obtained as the main product.

When a phenoxy alicyclic monocarboxylic acid derivative (Ia) (i.e., A' = H) and a phenoxy alicyclic dicarboxylic acid derivative (Ia)

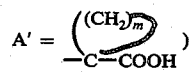

are produced at the same time, they can be separated from each other by a usual purification method such as recrystallization or chromatography.

The reaction may be carried out in the presence of excess chloroform and the keto-compound (III) in the presence or absence of an inert reaction medium. Examples of the reaction medium include dioxane, benzene, toluene, etc.

Bisphenol derivatives of the formula (II) employed as starting material can be obtained by a method disclosed, for example, in J.A.C.S., 61, 345 (1939). In this case bisphenol derivatives of the formula (II) represent 1,1-bis(4'-hydroxyphenyl)cyclopentane, 1,1-bis(4'-hydroxyphenyl)cyclohexane and 1,1-bis(4'-hydroxyphenyl)cycloheptane. The keto-compounds of the formula (III) represent cyclopentanone, cyclohexanone and cycloheptanone.

Procedure 2

Condensation reaction of a bisphenol-derivative (II) with an α-halogeno- or hydroxy-alicyclic carboxylic acid derivative (IV)

When X is halogen, 1 mole of a bisphenol derivative (II) is dissolved or suspended in an inert reaction medium and contacted with at least 1 mole of an alkaline agent to form an alkaline salt, and then at least 1 mole of an α-halogenated alicyclic acid derivative (IV) (i.e., X = halogen) is added into the resultant reaction mixture to effect the condensation reaction. When reaction is completed, the reaction mixture is further subjected to the usual purification procedures to give the desired phenoxy alicyclic carboxylic acid derivative (I). Examples of the inert reaction medium used in this process include benzene, toluene, methanol, ethanol, ether, dioxane, dimethylsulfoxide, N,N-dimethylformamide, etc. Examples of the alkaline agent used include potassium hydroxide, sodium hydroxide, alkali metal alcoholates, alkali metal carbonates, metallic sodium, sodium hydride and organic tertiary amines such as trimethylamine, triethylamine and pyridine. The reaction requires a temperature of 20° – 120° C.

In order to obtain, as the chief product, either a phenoxy alicyclic monocarboxylic acid derivative (I) (i.e., A = H) or a phenoxy alicyclic dicarboxylic acid derivative (I) (i.e.,

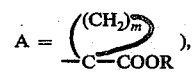

the reaction conditions such as the proportions of the reactants, the reaction temperature and the reaction time should be carefully controlled. If the alkaline agent and/or the α-halogeno alicyclic acid derivative (IV) are used in an equimolar amount of the bisphenol derivative (II), a phenoxy alicyclic monocarboxylic acid derivative (I) (i.e., A = H) is mainly obtained. On the other hand, if two or more mols of both the alkaline agent and the α-halogeno-alicyclic acid derivative (IV) are used per mole of the bisphenol derivative (II), a phenoxy alicyclic dicarboxylic acid derivative (I) (i.e.,

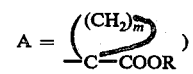

is mainly obtained.

When X is a hydroxyl group, 1 mole of a bisphenol derivative (II) is contacted with at least 1 mole of an α-hydroxy alicyclic acid derivative (IV) (i.e., X = OH) in the presence of an acidic catalyst such as sulfuric acid, p-toluenesulfonyl chloride, arsenic acid, boric acid, sodium hydrogen sulfate, potassium hydrogen sulfate, etc. in the presence or absence of an inert reaction medium. Examples of the reaction medium used include benzene, toluene, dioxane, etc. The acid catalyst is used in an amount of 0.01 – 0.5 mole per 1 mole of a bisphenol derivative. The reaction requires a temperature of 10° –90° C.

In order to obtain, as the chief product, either a phenoxy alicyclic monocarboxylic acid derivative (I) (i.e., A = H) or a phenoxy alicyclic dicarboxylic acid derivative (I) (i.e.,

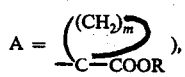

as described above, the reaction conditions such as the proportions of the reactants, the reaction temperature and the reaction time should be carefully controlled.

A phenoxy alicyclic carboxylic acid derivative (Ia) or its reactive ester is converted into an ester by usual esterification procedures, for example, by treatment with an esterifying agent. In this process, the term "reactive ester" of the phenoxy alicyclic carboxylic acid derivative (Ia) means an acyl halide, an acid anhydride, an ester of the acid, a salt of the acid, etc. and the term "esterification agent" means an alcohol, diazomethane, a dialkyl sulfate, an alkyl halide, an alkyl halogenosulfite, etc.

In the present invention, the phenoxy alicyclic carboxylic acid derivative (I) wherein R is hydrogen and/or A is hydrogen can be converted to a salt by treatment with an alkali. The salt is formed at the carboxyl and/or phenolic hydroxyl. An alkali metal salt can be obtained by contacting the phenoxy alicyclic carboxylic acid derivative (I) wherein R is hydrogen and/or A is hydrogen with sodium hydroxide, potassium hydroxide, sodium carbonate, potassium carbonate, sodium bicarbonate or ammonia, etc., or with an alcoholate of an alkali metal such as sodium methylate in an organic solvent, preferably in a lower alkanol such as methanol or ethanol, or with hydroxide, carbonate or bicarbonate of an alkali metal in an organic solvent, preferably in acetone or methanol, if necessary in the presence of a small amount of water. The alkali metal salt thus obtained can be converted to an alkaline earth metal salt by treatment with a salt of an alkaline earth metal such as calcium chloride.

According to the present invention, the following phenoxy alicyclic carboxylic acid derivatives are obtained.

Cyclo $C_5H_8$-1,1-[p-$C_6H_4OC(CH_2)_4CO_2H$]$_2$
Cyclo $C_5H_8$-1,1-[p-$C_6H_4OC(CH_2)_5CO_2H$]$_2$
Cyclo $C_5H_8$-1,1-[p-$C_6H_4OC(CH_2)_6CO_2H$]$_2$
Cyclo $C_6H_{10}$-1,1-[p-$C_6H_4OC(CH_2)_4CO_2H$]$_2$
Cyclo $C_6H_{10}$-1,1-[p-$C_6H_4OC(CH_2)_5CO_2H$]$_2$
Cyclo $C_6H_{10}$-1,1-[p-$C_6H_4OC(CH_2)_6CO_2H$]$_2$
Cyclo $C_7H_{12}$-1,1-[p-$C_6H_4OC(CH_2)_4CO_2H$]$_2$
Cyclo $C_7H_{12}$-1,1-[p-$C_6H_4OC(CH_2)_5CO_2H$]$_2$
Cyclo $C_7H_{12}$-1,1-[p-$C_6H_4OC(CH_2)_6CO_2H$]$_2$
Cyclo $C_5H_8$-1,1-(B)p-$C_6H_4OC(CH_2)_4CO_2H$
Cyclo $C_5H_8$-1,1-(B)p-$C_6H_4OC(CH_2)_5CO_2H$
Cyclo $C_5H_8$-1,1-(B)p-$C_6H_4OC(CH_2)_6CO_2H$
Cyclo $C_6H_{10}$-1,1-(B)p-$C_6H_4OC(CH_2)_4CO_2H$
Cyclo $C_6H_{10}$-1,1-(B)p-$C_6H_4OC(CH_2)_5CO_2H$
Cyclo $C_6H_{10}$-1,1-(B)p-$C_6H_4OC(CH_2)_6CO_2H$
Cyclo $C_7H_{12}$-1,1-(B)p-$C_6H_4OC(CH_2)_4CO_2H$
Cyclo $C_7H_{12}$-1,1-(B)p-$C_6H_4OC(CH_2)_5CO_2H$
Cyclo $C_7H_{12}$-1,1-(B)p-$C_6H_4OC(CH_2)_6CO_2H$
Methyl esters of the above-mentioned acids
Ethyl esters of the above-mentioned acids
n-Propyl esters of the above-mentioned acids
iso-Propyl esters of the above-mentioned acids
n-Butyl esters of the above-mentioned acids
iso-Butyl esters of the above-mentioned acids
t-Butyl esters of the above-mentioned acids
Na salts of the above-mentioned acids
K salts of the above-mentioned acids
Ca salts of the above-mentioned acids
Mg salts of the above-mentioned acids
$NH_4$ salts of the above-mentioned acids
Al salts of the above-mentioned acids In the above examplified compounds, "B" means a group of the formula

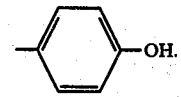

The present invention further provides a pharmaceutical composition containing a phenoxy alicyclic carboxylic acid derivative of the formula,

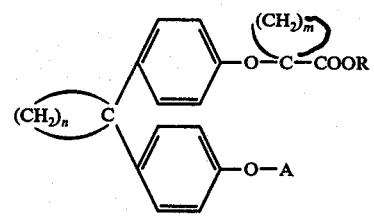

wherein R is hydrogen or $C_1$-$C_4$ alkyl, n and m each signify an integer of 4 to 6, and A represents hydrogen or a group of the formula,

wherein R and m have the same meanings as defined above, and at least one pharmaceutically acceptable carrier.

The present phenoxy alicyclic carboxylic acid derivatives (I) may be used with or without admixing at least one pharmaceutically acceptable carrier, for instance, lactose, potato starch, corn starch, cellulose derivatives, gelatin, corn oil, cotton seed oil etc., in the form of capsules, tablets, powder or the like.

The cholesterol-lowering agents of this invention may be, for example, orally administered. Usually the amount orally administered is 0.01 g. - 10 g. per day/human adult, preferably 0.05 g. - 3 g. per day/human adult. The cholesterol-lowering agent may be in any suitable form which is conventional for oral administration. Thus, it may be encased in a capsule, or it may be in a liquid form, in a tablet form, or in a powder form. In preparing the agents in these various forms, the active compound may be mixed with or impregnated in a suitable solid carrier.

The cholesterol-lowering activity of the present compounds was tested as follows:

Male mice weighing 15 to 18 g. obtained from NIHON ANIMALS CO. were fed on a normal commercial chow pellet. They were divided into experimental groups, 6 animals or more in each group, and intravenously injected with 500 mg/kg of Triton WR 1339 (Trademark for oxyethylated tert-octylphenol formaldehyde polymer manufactured by Rohm & Haas Co., U.S.A.). The test compounds were administered orally in a dose of 50 mg/kg immediately after the Triton injection. One group of mice was injected with Triton and received vehicle only (without test compound) and served as a Triton injected control and another group receiving no treatment served as a normal control. 24 Hours after the Triton injection, mice were sacrificed for analysis of serum cholesterol.

Cholesterol-lowering activity is expressed as follows:

$$\frac{[\text{Triton injected control}] - [\text{Treated mice}]}{[\text{Triton injected control}] - [\text{Normal control}]} \times 100$$

where the brackets mean serum cholesterol levels. For example, [Triton injected control] is a mean value of serum cholesterol levels (mg/dl) of Triton injected control group.

An example of the results obtained in this test is shown in Table 1. In Table 1 compounds are referred to by number of the Examples.

Table 1

| Compounds (No.) | Cholesterol-lowering effect (%) |
|---|---|
| 1 | 74 |
| 2 | 72 |
| 3 | 71 |
| 4 | 93 |
| 5 | 94 |
| 6 | 32 |
| 7 | 35 |
| 8 | 72 |
| Clofibrate* | 17 |

(*Trademark for ethyl-p-chlorophenoxyisobutyrate produced by I.C.I.)

Phenoxy alicyclic monocarboxylic acid derivatives have a tendency of hypertrophy of liver than phenoxy alicyclic dicarboxylic acid derivatives.

The present invention will be illustrated in more detail with reference to the following examples, which are only illustrative, but not limitative.

EXAMPLE 1

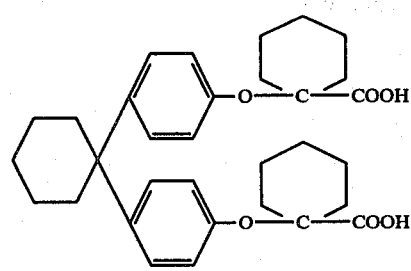

To a mixture of 15 g. of 1,1-bis(4'-hydroxyphenyl)cyclohexane and 300 g. of cyclohexanone was added 75 g. of potassium hydroxide. Then 40 g. of chloroform was added to the mixture with stirring at 20° - 30° C., and the mixture was heated at 60° - 70° C for 3 hours to complete the reaction. Thereafter the reaction mixture was concentrated to give a residue. After the residue was dissolved in water, the solution was treated with activated charcoal and acidified by dilute hydrochloric acid to give an oily substance. The oily substance was extracted with ether and the ether solution was extracted again with an aqueous dilute $Na_2CO_3$ solution. The separated alkaline aqueous layer was acidified and extracted with ether. The ether layer was dried over anhydrous sodium sulfate and concentrated to give a crude product, which was purified by recrystallization from toluene. The desirable phenoxy alicyclic dicarboxylic acid was obtained, 12 g., m.p. 174° - 175° C.

Elementary analysis: Calculated (%) C: 73.82 H: 7.74
Found (%) C: 73.52 H: 7.61

EXAMPLES 2 - 5

According to a procedure similar to that disclosed in Example 1, the following compounds were obtained as shown in Table 2.

Table 2

| Ex. | Starting material | | | KOH or NaOH g | CHCl₃ g (temp.) | Reaction time hours (temp.) | Product Chemical Structure | Physical property | Elementary analysis Calculated (%) | Found (%) |
|---|---|---|---|---|---|---|---|---|---|---|
| | (bisphenol with cyclic (CH₂)ₙ bridge) OH...OH | (CH₂)ₘ C=O g | | | | | | | | |
| 2 | [4-OH-C₆H₄-]₂C(cyclohexyl) 10 g | cyclopentanone 200 g | | KOH | 27 g (20°–30° C) | 4 (60°–70° C) | bis(tetrahydropyran carboxylic acid) derivative 12 g | m.p. 190°–1° C (from toluene) | C 73.14 H 7.39 | 73.19 7.49 |
| 3 | [4-OH-C₆H₄-]₂C(cyclohexyl) 10 g | cyclohexanone 200 g | | 50 g KOH | 25 g (20°–30° C) | 3 (60°–70° C) | derivative | m.p. 180.5°–2° C (from toluene) | C 75.27 H 7.74 | 75.11 7.78 |
| 4 | [4-OH-C₆H₄-]₂C(cyclohexyl) 10 g | cyclopentanone 200 g | | 50 g KOH | 15 g (20°–30° C) | 3 (60°–70° C) | derivative 5 g | m.p. 196°–9° C | C 75.76 H 7.42 | 75.48 7.44 |
| 5 | [4-OH-C₆H₄-]₂C(cyclohexyl) 20 g | cyclohexanone 400 g | | 45 g KOH | CHCl₃ 12 g (20°–30° C) | 3 (60°–70° C) | derivative 14 g | m.p. 199°–201° C (from toluene) | C 76.11 H 7.67 | 75.81 7.76 |
| | 15 g | 250 g | | 36 g | | | 9 g | | | |

EXAMPLE 6

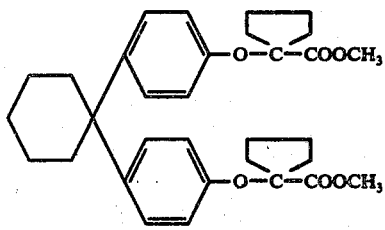

To a mixture of 2 g. of 1,1-bis(4'-hydroxyphenyl)cyclohexane and 20 ml. of dry toluene was added 0.6 g. of sodium methoxide. Then 3.5 g. of 1-bromocyclopentylcarboxylic acid methyl ester dissolved in toluene was gradually added dropwise to the mixture with stirring. The mixture was heated at 60° – 80° C for 6 hours. The reaction mixture was then washed with water. Thereafter, toluene was distilled off, and the residue was purified in chromatography column packed with activated alumina. The desirable ester was obtained, 2.5 g., m.p. 119° – 122° C.

Elementary analysis: Calculated (%) C: 73.82 H: 7.74 Found (%) C: 73.77 H: 7.81

EXAMPLE 7

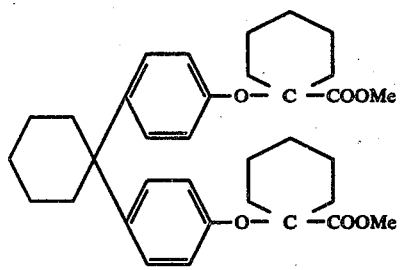

To a mixture of 3 g. of 1,1-bis(4'-hydroxyphenyl)cyclohexane and 30 ml. of dry toluene was added a toluene suspension of sodium hydride under cooling. After stirring the mixture for half an hour, a mixture of 5 g. of 1-bromocyclohexylcarboxylic acid methyl ester and 10 ml. of dry toluene was added dropwise, and the mixture was heated with stirring for 6 hours. After cooling, the reaction mixture was washed with water. The toluene was distilled off. The residue was purified by recrystallization. The desirable ester was obtained, 3.6 g., m.p. 104° – 107° C.

Elementary analysis: Calculated (%) C: 74.42 H: 8.08 Found (%) C: 74.31 H: 8.10

EXAMPLE 8

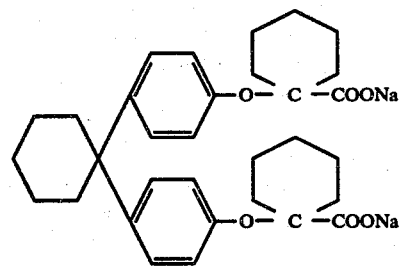

The dicarboxylic acid obtained in Example 1 was treated with a 10% NaOH aqueous solution with gentle heating to yield colorless plates which were slightly soluble in water, m.p. > 260° C.

What is claimed is:
1. A compound of the formula,

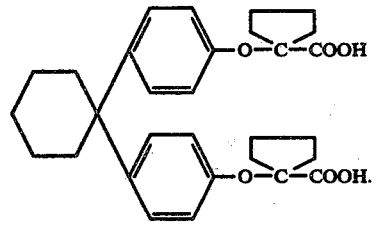

* * * * *